United States Patent
Watanabe

(10) Patent No.: US 9,952,243 B2
(45) Date of Patent: Apr. 24, 2018

(54) REAGENT VESSEL HOUSING UNIT AND AUTOMATIC ANALYSIS DEVICE

(71) Applicants: JEOL Ltd., Tokyo (JP); Fujirebio Inc., Tokyo (JP)

(72) Inventor: Takashi Watanabe, Tokyo (JP)

(73) Assignees: JEOL Ltd., Tokyo (JP); Fujirebio Inc., Tokyo (JP)

( * ) Notice: Subject to any disclaimer, the term of this patent is extended or adjusted under 35 U.S.C. 154(b) by 0 days.

(21) Appl. No.: 15/126,613

(22) PCT Filed: Mar. 13, 2015

(86) PCT No.: PCT/JP2015/057578
§ 371 (c)(1),
(2) Date: Sep. 16, 2016

(87) PCT Pub. No.: WO2015/141599
PCT Pub. Date: Sep. 24, 2015

(65) Prior Publication Data
US 2017/0082647 A1 Mar. 23, 2017

(30) Foreign Application Priority Data
Mar. 20, 2014 (JP) .................................. 2014-058292

(51) Int. Cl.
*G01N 35/04* (2006.01)
*G01N 35/00* (2006.01)

(52) U.S. Cl.
CPC ... *G01N 35/04* (2013.01); *G01N 2035/00435* (2013.01); *G01N 2035/0405* (2013.01); *G01N 2035/0443* (2013.01); *G01N 2035/0453* (2013.01)

(58) Field of Classification Search
None
See application file for complete search history.

(56) References Cited

FOREIGN PATENT DOCUMENTS

| DE | 3307764 A1 | 9/1983 |
|----|------------|--------|
| EP | 1918721 A1 | 5/2008 |
| JP | 720132 A | 1/1995 |
| JP | 2004156971 A | 6/2004 |
| JP | 2004157020 A | 6/2004 |
| JP | 200740900 A | 2/2007 |
| JP | 2010107449 A | 5/2010 |
| JP | 201432099 A | 2/2014 |
| WO | 9609554 A1 | 3/1996 |

OTHER PUBLICATIONS

Machine-generated English translation of JP 2010-107449, published May 13, 2010.*
Machine-generated English translation of JP 2004-156971, published Jun. 3, 2004.*

* cited by examiner

*Primary Examiner* — P. Kathryn Wright
(74) *Attorney, Agent, or Firm* — The Webb Law Firm

(57) ABSTRACT

A reagent vessel housing unit 7 is provided with a drive unit 121 for a base member 122. The base member supports a first opening/closing mechanism 135 for a first reagent vessel and a second opening/closing mechanism 136 for a second reagent vessel. The drive unit 121 positions the base member 122 at an initial position, at a position at which the cap of a first reagent vessel and the cap of a second reagent vessel are closed, at a first opening position at which the cap of the first reagent vessel is opened, and at a second opening position at which the cap of the second reagent vessel is opened.

5 Claims, 12 Drawing Sheets

REAGENT VESSEL HOUSING UNIT AND AUTOMATIC ANALYSIS DEVICE

CROSS-REFERENCE TO RELATED APPLICATIONS

This application is the United States national phase of International Application No. PCT/JP2015/057578 filed Mar. 13, 2015, and claims priority to Japanese Patent Application No. 2014-058292 filed Mar. 20, 2014, the disclosures of which are hereby incorporated in their entirety by reference.

TECHNICAL FIELD

The present invention relates to a reagent vessel housing unit that houses reagent vessels, and an automatic analysis device that includes the reagent vessel housing unit.

BACKGROUND ART

An automatic analysis device is used in tests in various fields, such as in immunological tests, biochemical tests, and blood transfusion tests; performs analytical processing on multiple samples at the same time; and analyzes multiple components quickly with high precision. The automatic analysis device includes a reagent vessel housing unit that houses a reagent vessel that houses a reagent used in tests.

In order to prevent a reagent from evaporating or deteriorating, a reagent vessel provided with an openable/closable cap is proposed. The cap of the reagent vessel is opened only when the reagent is sucked, and is closed at other times. Patent Literature 1 discloses a reagent vessel housing unit in which a mechanism that opens and closes a cap of a reagent vessel is provided at a cover member.

In immunological tests, as reagents used in tests, two types of reagents, that is, a magnetic reagent and a labeling reagent, are required. Therefore, in recent years, a reagent vessel housing unit that is capable of housing two types of reagent vessels has been proposed. The two types of reagents are sucked at respective suction positions that differ from each other.

CITATION LIST

Patent Literature

PTL 1: Japanese Unexamined Patent Application Publication No. 2007-40900

SUMMARY OF INVENTION

Technical Problem

However, in the technology described in Patent Literature 1, one drive unit is driven for opening and closing the cap of one reagent vessel. Therefore, in order to open and close the caps of two reagent vessels, two drive units are required. As a result, a plurality of drive units are required at the cover member. This not only increases the number of components, but also increases power consumption.

Considering the aforementioned problems, it is an object of the present invention to provide a reagent vessel housing unit and an automatic analysis device that are capable of opening and closing caps of two reagent vessels by one drive unit.

Solution to Problem

In order to solve the aforementioned problems and realize the object of the present invention, a reagent vessel housing unit according to the present invention comprises a housing, a hollow cover member, a drive unit, a base member, a first opening/closing mechanism, and a second opening/closing mechanism. The housing houses a first reagent vessel and a second reagent vessel and has an opening portion, the first reagent vessel and the second reagent vessel each having a cap. The hollow cover member includes a bottom surface portion that covers the opening portion of the housing. The drive unit is disposed in the cover member. The base member is movable to an initial position, a first opening position, and a second opening position by a driving force of the drive unit, the initial position being where the cap of the first reagent vessel and the cap of the second reagent vessel are closed, the first opening position being where the cap of the first reagent vessel is opened, the second opening position being where the cap of the second reagent vessel is opened. The first opening/closing mechanism is operated by the base member and opens the cap of the first reagent vessel when the base member has moved to the first opening position. The second opening/closing mechanism is operated by the base member and opens the cap of the second reagent vessel when the base member has moved to the second opening position.

An automatic analysis device comprises a reagent vessel housing unit that houses a first reagent vessel that houses a first reagent and a second reagent vessel that houses a second reagent; and a reaction unit that sucks the first reagent and the second reagent and that causes a reaction of the first reagent and the second reagent with a sample to occur. The reagent vessel housing unit includes a housing, a hollow cover member, a drive unit, a base member, a first opening/closing mechanism, and a second opening/closing mechanism. The housing houses a first reagent vessel and a second reagent vessel and has an opening portion, the first reagent vessel and the second reagent vessel each having a cap. The hollow cover member includes a bottom surface portion that covers the opening portion of the housing. The drive unit is disposed in the cover member. The base member is movable to an initial position, a first opening position, and a second opening position by a driving force of the drive unit, the initial position being where the cap of the first reagent vessel and the cap of the second reagent vessel are closed, the first opening position being where the cap of the first reagent vessel is opened, the second opening position being where the cap of the second reagent vessel is opened. The first opening/closing mechanism is operated by the base member and opens the cap of the first reagent vessel when the base member has moved to the first opening position. The second opening/closing mechanism is operated by the base member and opens the cap of the second reagent vessel when the base member has moved to the second opening position.

Advantageous Effects of Invention

According to the reagent vessel housing unit and the automatic analysis device according to the present invention, it is possible to independently open and close the caps of two reagent vessels as a result of moving the base member to three positions, that is, the initial position, the first opening position, and the second opening position.

DESCRIPTION OF EMBODIMENTS

Figure 1:
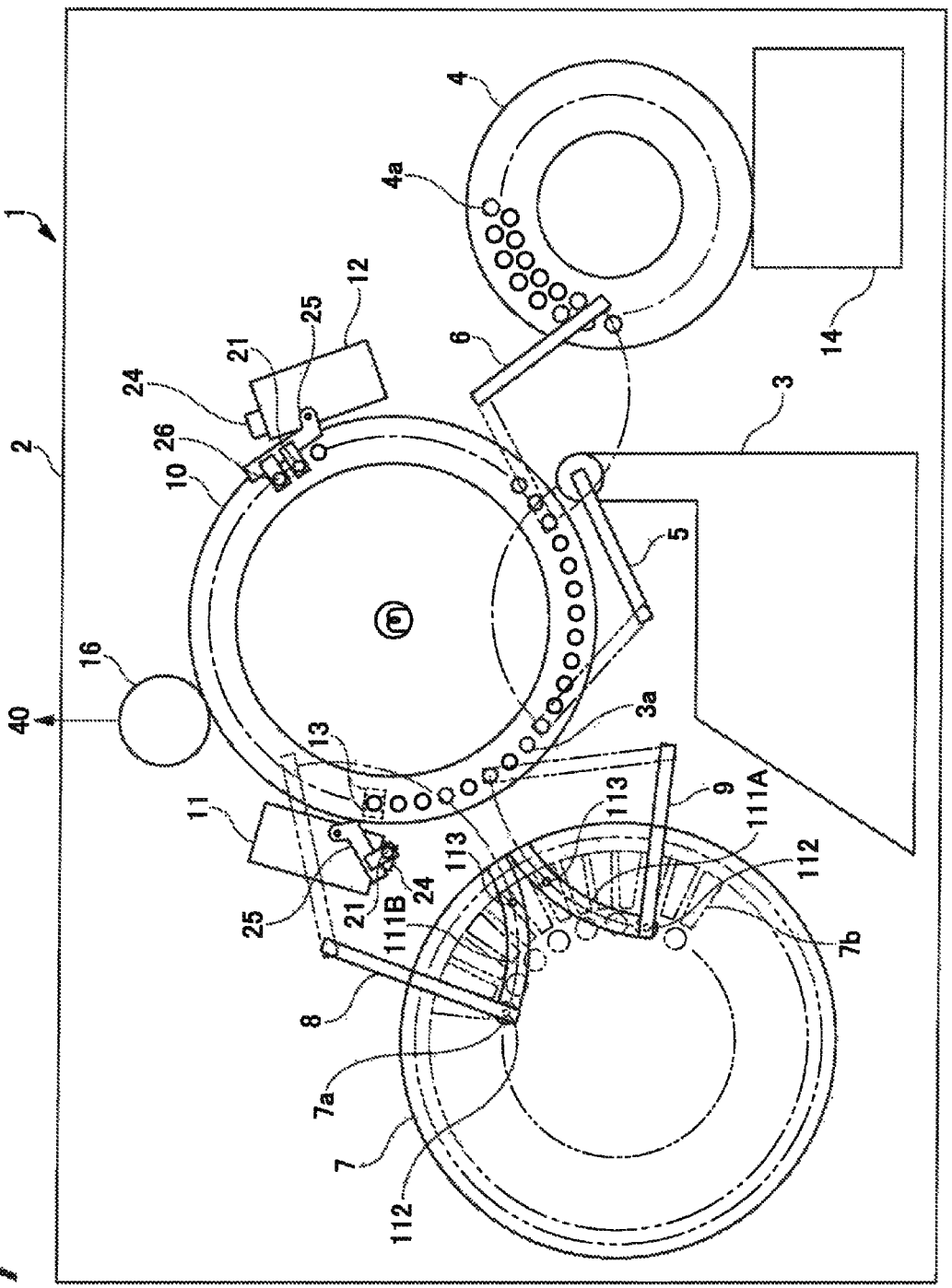
FIG. 1 is a schematic structural view of an automatic analysis device according to an embodiment of the present invention.

An automatic analysis device and a reagent vessel housing unit according to an embodiment of the present invention are hereunder described with reference to FIGS. 1 to 12. In the figures, common members are given the same reference numerals. The description is given in the following order. The present invention is not necessarily limited to the following forms.

1. First Embodiment
1-1. Structure of Automatic Analysis Device
1-2. Structure of Reagent Vessel Housing Unit
2. Operations of Reagent Vessel Housing Unit 1. First Embodiment 1-1. Structure of Automatic Analysis Device First, an automatic analysis device according to a first embodiment of the present invention is described with reference to FIG. 1.

FIG. 1 is a schematic explanatory view of the automatic analysis device according to the embodiment.

The automatic analysis device 1 shown in FIG. 1 is applied to an immunology analysis device that performs immunology analysis of, for example, an antigen-antibody reaction of a sample. The automatic analysis device 1 includes a measuring device 2 and a controlling device 40 that controls the entire automatic analysis device 1 including the measuring device 2 and that analyzes measurement data that is output from the measuring device 2.

The automatic analysis device 1 that is applied to an immunology analysis device performs measurements with high sensitivity by using, for example, Chemiluminescent Enzyme Immunoassay (CLEIA). The main steps of CLEIA include a reaction step of reacting a sample (antigen or antibody) and a reagent in a reactor vessel, a separating step (BF separation) of separating a reaction product (bound) and an unreacted substance (free) from each other in the reactor vessel, and a photometric measuring step of the emission quantity of light generated from an immune complex that is generated when each reagent and the sample react with each other.

[Measuring System of Automatic Analysis Device 1]

The measuring device 2 roughly includes a reactor vessel supplying unit 3, a sample installing unit 4, a reactor vessel transporting unit 5, a sample dispensing unit 6, a reagent vessel housing unit 7, a first reagent dispensing unit 8, a second reagent dispensing unit 9, an immune enzyme reaction unit 10, a first BF separating unit 11, a second BF separating unit 12, a substrate liquid cooler 14 and a detector 16.

The reactor vessel supplying unit 3 houses a plurality of reactor vessels (cuvettes) 3a, and supplies the plurality of reactor vessels 3a one at a time to a transfer position. The reactor vessel 3a supplied to the transfer position is transported to the immune enzyme reaction unit 10 by the reactor vessel transporting unit 5. A sample and a predetermined reagent are injected into the reactor vessel 3a transported to the immune enzyme reaction unit 10.

The reactor vessel transporting unit 5 includes an arm and a holding unit. The arm moves up and down in vertical directions and is rotatable around a vertical line that extends through a base end portion of the arm and that serves as a center axis. The holding unit is provided at an end portion of the arm. In the reactor vessel transporting unit 5, the reactor vessel 3a supplied to a supply position of the reactor vessel supplying unit 3 is held by the holding unit, and the arm rotates, so that the reactor vessel 3a is transported to a predetermined position on the immune enzyme reaction unit 10 at a predetermined timing.

The sample installing unit 4 includes a turntable having the form of a substantially cylindrical vessel that is open at one end in an axial direction. The sample installing unit 4 houses a plurality of sample vessels 4a. The sample vessels 4a house samples of blood, urine, or the like, taken from an examinee. The plurality of sample vessels 4a are disposed side by side and apart from each other with predetermined intervals therebetween in a peripheral direction of the sample installing unit 4. The sample installing unit 4 is supported so as to be rotatable along the peripheral direction by a drive mechanism (not shown). The sample installing unit 4 is rotated at a predetermined speed for each predetermined angular range in the peripheral direction by the drive mechanism (not shown). In the embodiment shown in FIG. 1, the sample vessels 4a that are arranged side by side in the peripheral direction of the sample installing unit 4 are provided in two rows that are apart from each other with a predetermined interval therebetween in a radial direction of the sample installing unit 4. As the sample, a sample diluted by a predetermined diluent may be used.

The sample dispensing unit 6 includes an arm and a probe. The arm moves up and down in vertical directions and is rotatable around a vertical line that extends through a base end portion of the arm and that serves as a center axis. The probe is provided at an end portion of the arm. In the sample dispensing unit 6, the probe sucks the sample in the sample vessel 4a moved to a predetermined position on the sample installing unit 4, and the arm rotates, so that the sample is dispensed into the reactor vessel 3a that is at the predetermined position on the immune enzyme reaction unit 10 at a predetermined timing.

The reagent vessel housing unit 7 houses a first reagent vessel 7a and a second reagent vessel 7b. The first reagent vessel 7*a* houses, as a first reagent, a magnetic reagent in which magnetic particles to whose surfaces an antibody that reacts with a target antigen in the sample are fixed are dispersed in a liquid. The second reagent housing vessel 7*b* houses, as a second reagent, a labeling reagent (enzyme antibody) that reacts with a reaction product in which the magnetic reagent and the antigen in the sample are combined with each other. The interior of the reagent vessel housing unit 7 is maintained at a predetermined temperature by a cold reserving mechanism (not shown). Therefore, the first reagent (magnetic reagent) housed in the first reagent vessel 7*a* and the second reagent (labeling reagent) housed in the second reagent vessel 7*b* are kept cool at a predetermined temperature. The structure of the reagent vessel housing unit 7 is described in more detail below.

The first reagent dispensing unit 8 includes an arm and a probe. The arm moves up and down in vertical directions and is rotatable around a vertical line that extends through a base end portion of the arm and that serves as a center axis. The probe is provided at an end portion of the arm. In the first reagent dispensing unit 8, the probe sucks the first reagent (magnetic reagent) in the first reagent vessel 7*a* moved to a predetermined position on the reagent vessel housing unit 7 or the second reagent (labeling reagent) in the second reagent vessel 7*b* moved to the predetermined position on the reagent vessel housing unit 7. In the first reagent dispensing unit 8, the arm is rotated, so that the first reagent or the second reagent is dispensed into the reactor vessel 3*a* that is at the predetermined position on the immune enzyme reaction unit 10 at a predetermined timing.

The structure of the second reagent dispensing unit 9 is the same as the structure of the first reagent dispensing unit 8. In the second reagent dispensing unit 9, a probe sucks the first reagent (magnetic reagent) in the first reagent vessel 7*a* moved to a predetermined position on the reagent vessel housing unit 7 or the second reagent (labeling reagent) in the second reagent vessel 7*b* moved to the predetermined position on the reagent vessel housing unit 7. In the second reagent dispensing unit 9, the arm is rotated, so that the first reagent or the second reagent is dispensed into the reactor vessel 3*a* that is at the predetermined position on the immune enzyme reaction unit 10 at a predetermined timing.

At the immune enzyme reaction unit 10, an immune reaction between the sample and a predetermined reagent corresponding to analysis items occurs in the reactor vessel 3*a* disposed in a peripheral direction, and an enzyme reaction between an immune complex that is generated by the immune reaction and a chemiluminescent substrate occurs. As with the sample installing unit 4, the immune enzyme reaction unit 10 includes a turntable having the form of a substantially cylindrical vessel that is open at one end in an axial direction. The immune enzyme reaction unit 10 is supported so as to be rotatable along the peripheral direction by a drive mechanism (not shown). The immune enzyme reaction unit 10 is rotated at a predetermined speed for each predetermined angular range in the peripheral direction thereof by the drive mechanism (not shown). Here, the immune enzyme reaction unit 10 rotates counterclockwise. In the embodiment shown in FIG. 1, the reactor vessels 3*a* that are arranged side by side in the peripheral direction of the immune enzyme reaction unit 10 are provided in one row as a set and apart from each other with predetermined intervals therebetween in a radial direction of the immune enzyme reaction unit 10. However, it is possible to provide a row of reactor vessels 3*a* for the first reagent (described later) and a row of reactor vessels 3*a* for the second reagent (described later) apart from each other with a predetermined interval therebetween in the radial direction.

When the first reagent dispensing unit 8 dispenses the magnetic reagent into the reactor vessel 3*a* into which the sample has been injected, the immune enzyme reaction unit 10 stirs a liquid mixture containing the magnetic reagent and the sample by an stirring mechanism (not shown), so that an immune reaction between the magnetic reagent and the antigen in the sample occurs for a certain period of time (primary immune reaction). Next, the immune enzyme reaction unit 10 causes this reactor vessel 3*a* to move to a first magnetism collecting mechanism (magnets 13), so that a reaction product in which the antigen and the magnetic reagent have combined with each other is subjected to a magnetism collecting operation by a magnetic force. Then, in this state, the interior of the reactor vessel 3*a* is cleaned to remove any unreacted substances that did not react with the magnetic reagent (primary BF separating operation).

The first magnetism collecting mechanism is fixed to a position that corresponds to the position of the first BF separating unit 11 disposed in the vicinity of an outer peripheral portion of the immune enzyme reaction unit 10. The turntable of the immune enzyme reaction unit 10 includes two layers, that is, a fixed lower layer and a rotatable upper layer. Two magnets 13 serving as the first magnetism collecting mechanism are disposed at the turntable at the lower layer, and the reactor vessel 3*a* is disposed at the turntable at the upper layer. The two magnets 13 oppose each other so as to be disposed on both sides of the reactor vessels 3*a*, and perform a magnetism collecting operation on the reaction product in the reactor vessel 3*a* that has been moved to a location between the two magnets 13.

The first BF separating unit 11 includes an arm 25, a nozzle 21 mounted on the arm 25, and a cleaning tank 24. In a primary BF separating step, a cleaning liquid is discharged into and sucked by the reactor vessel 3*a* into which the sample and the magnetic reagent have been injected to clean the interior of this reactor vessel 3*a*, so that any unreacted substances that did not react with the magnetic reagent are removed (BF cleaning operation). The arm 25 moves up and down in vertical directions and is rotatable around a vertical line that extends through a base end portion of the arm and that serves as a center axis. The arm 25 moves the nozzle 21 to the reactor vessel 3*a* that is at a primary BF separation position at the immune enzyme reaction unit 10, and to the cleaning tank 24 at a nozzle cleaning position at a side of the first BF separating unit 11.

When the reactor vessel 3*a* is transported to the primary BF separation position, the first BF separating unit 11 performs the primary BF separating operation. By the primary BF separating operation and the BF cleaning operation, the reaction product in which the magnetic reagent and the target antigen in the sample have combined with each other is subjected to the magnetism collecting operation in the reactor vessel 3*a*. Then, when the primary BF separating operation ends, the nozzle 21 is moved to the nozzle cleaning position where the cleaning tank 24 is situated by the arm 25.

After the primary BF separating operation, when the second reagent dispensing unit 9 dispenses a labeling reagent into the reactor vessel 3*a* where the reaction product has remained, the immune enzyme reaction unit 10 stirs the liquid mixture containing the magnetic reagent and the sample by the stirring mechanism (not shown), so that an immune reaction between the reaction product and the labeling reagent occurs for a certain period of time (secondary immune reaction). Next, the immune enzyme reaction unit 10 causes the reactor vessel 3a to move to a second magnetism collecting mechanism (not shown), so that an immune complex in which the reaction product and the labeling reagent have combined with each other is subjected to a magnetism collecting operation by a magnetic force. Then, in this state, the interior of the reactor vessel 3a is cleaned to remove any unreacted substances that did not react with the labeling reagent (secondary BF separating operation).

Like the first magnetism collecting mechanism, the second magnetism collecting mechanism includes two magnets 13, and is fixed to a position that corresponds to the position of the second BF separating unit 12 disposed in the vicinity of the outer peripheral portion of the immune enzyme reaction unit 10. In the embodiment shown in FIG. 1, the two magnets 13 of the second magnetism collecting mechanism are disposed below a nozzle 21 that is at a secondary BF separation position.

The second BF separating unit 12 has a structure that is the same as that of the first BF separating unit 11, and is disposed apart from the first BF separating unit 11 with a predetermined distance therebetween in a peripheral direction. In a secondary BF separating step, a cleaning liquid is discharged into and sucked by the reactor vessel 3a into which the labeling reagent has been injected to clean the interior of this reactor vessel 3a, so that any excess unreacted substances that did not react with the labeling reagent are removed (BF cleaning operation). An arm 25 moves up and down in vertical directions and is rotatable around a vertical line that extends through a base end portion of the arm and that serves as a center axis. The arm 25 moves the nozzle 21 to the reactor vessel 3a that is at the secondary BF separation position at the immune enzyme reaction unit 10, and to the cleaning tank 24 at a nozzle cleaning position that is situated at a side of the second BF separating unit 12.

When the reactor vessel 3a is transported to the secondary BF separation position, the second BF separating unit 12 performs the secondary BF separating operation. By the secondary BF separating operation and the BF cleaning operation, the immune complex in which the labeling reagent and the reaction product containing the magnetic reagent and the target antigen in the sample have combined with each other is subjected to the magnetism collecting operation in the reactor vessel 3a. Then, when the secondary BF separating operation ends, the arm 25 moves the nozzle 21 to the nozzle cleaning position where the cleaning tank 24 is situated.

1-2. Structure of Reagent Vessel Housing Unit

Next, the structure of the reagent vessel housing unit 7 is described in more detail with reference to FIGS. 2 to 8.

Figure 2:
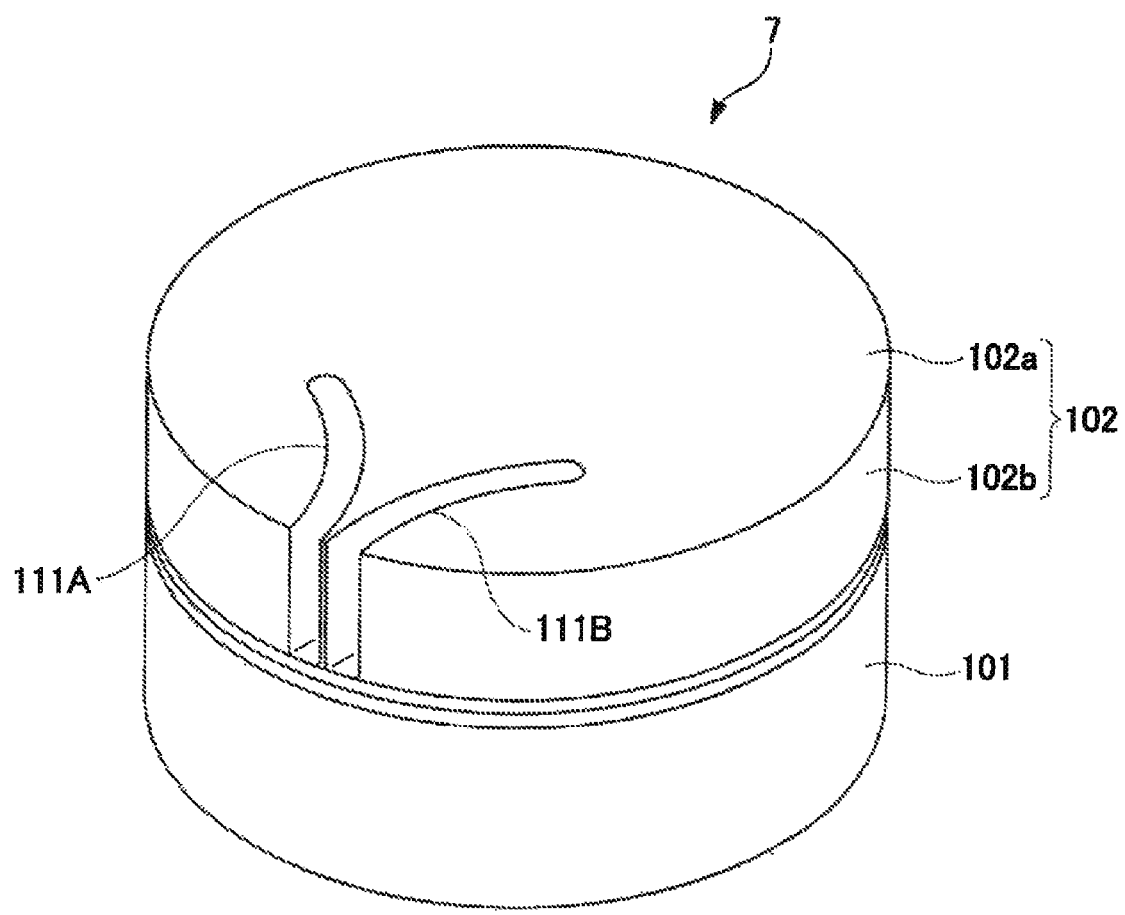
FIG. 2 is a perspective view of a reagent vessel housing unit according to the embodiment of the present invention.
Figure 3:
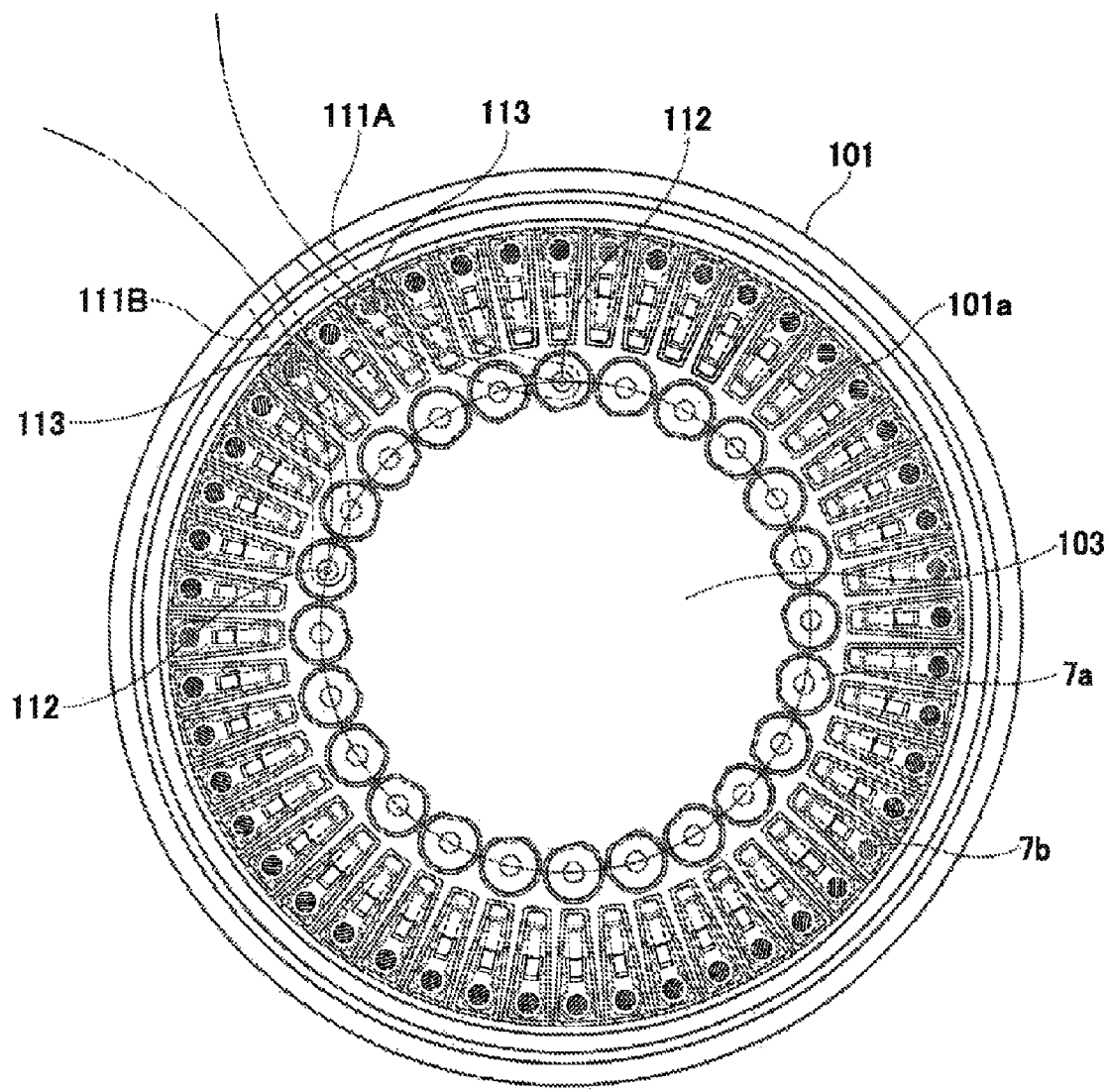
FIG. 3 is a plan view of the reagent vessel housing unit according to the embodiment of the present invention.
Figure 4:
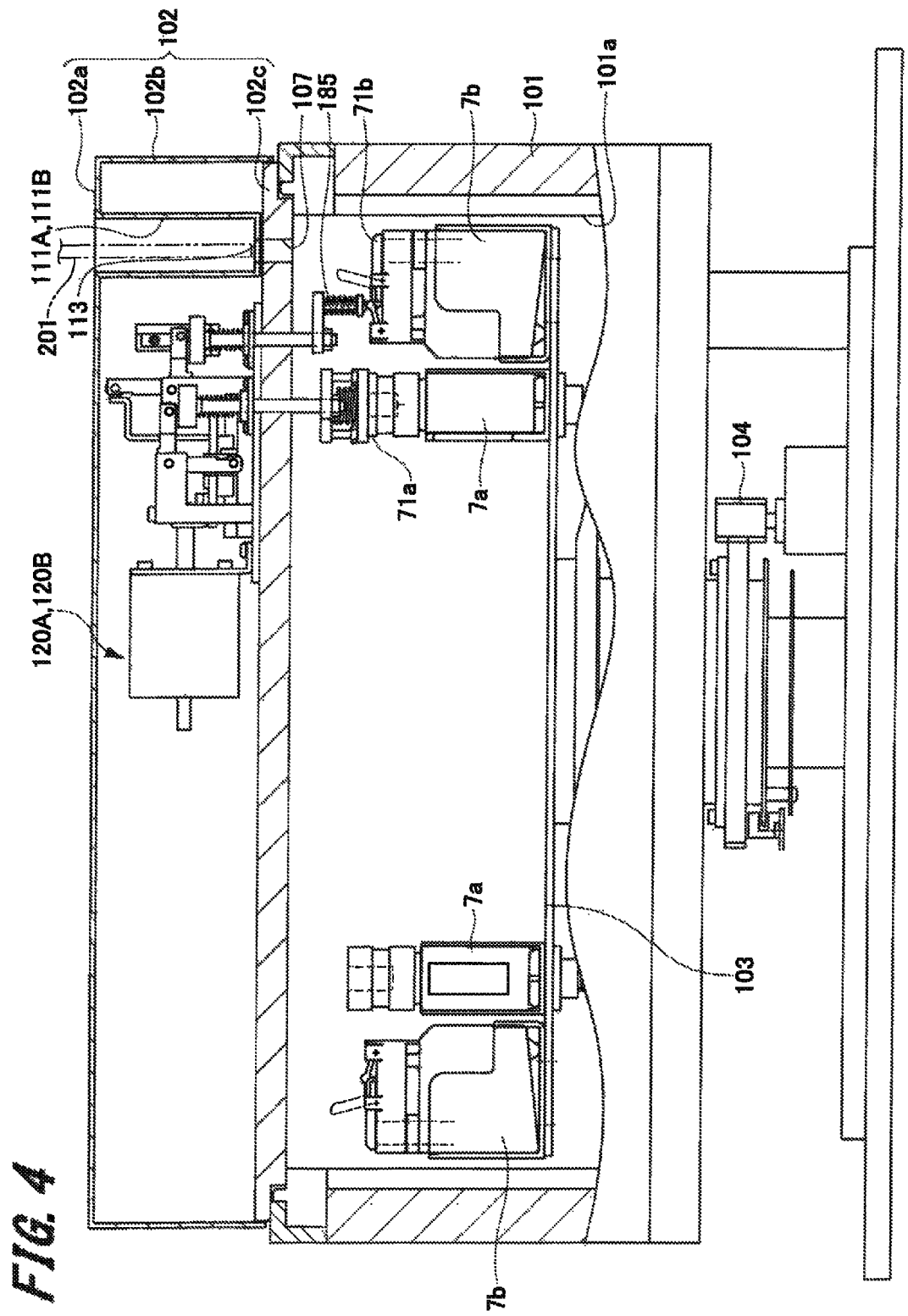
FIG. 4 is a sectional view of the reagent vessel housing unit according to the embodiment of the present invention.

FIG. 2 is a perspective view of the reagent vessel housing unit 7. FIG. 3 is a plan view of the reagent vessel housing unit. FIG. 4 is a sectional view of the reagent vessel housing unit 7.

As shown in FIG. 2, the reagent vessel housing unit 7 includes, for example, a housing 101 having the form of a substantially cylindrical vessel, a cover member 102 that covers an opening of the housing, a turntable 103 (see FIG. 4) disposed in the housing 101, and a table drive mechanism 104 (see FIG. 4).

As shown in FIGS. 3 and 4, the turntable 103 is housed in an internal space 101a of the housing 101. The first reagent vessel 7a and the second reagent vessel 7b are placed on the turntable 103. The first reagent vessel 7a and the second reagent vessel 7b are disposed apart from each other with a predetermined interval therebetween along a peripheral direction of the turntable 103. The housing 101 keeps the first reagent vessel 7a and the second reagent vessel 7b, which are housed in the internal space 101a, cool at a predetermined temperature. The first reagent vessel 7a has a cap 71a that opens when pushed downward along an up-down direction. Similarly, the second reagent vessel 7b has a cap 71b that opens when pushed downward in the up-down direction.

The turntable 103 is supported so as to be rotatable in the peripheral direction by the table drive mechanism 104. In addition, the turntable 103 is rotated in a normal direction or in a reverse direction at a predetermined speed for each predetermined angular range in the peripheral direction thereof by the table drive mechanism 104.

As shown in FIGS. 2 and 4, the cover member 102 has a hollow substantially cylindrical shape, with both ends in an axial direction being closed. The cover member 102 includes a substantially circular top surface portion 102a, a bottom surface portion 102c that opposes the top surface portion 102a and that covers the opening of the housing 101, and a side surface portion 102b that is substantially perpendicular to the top surface portion 102a and the bottom surface portion 102c. The cover member 102 has two grooved portions 111A and 111B through which a probe 201 that sucks a reagent passes. The two grooved portions 111A and 111B are continuously formed along the top surface portion 102a and the side surface portion 102b of the cover member 102, and are formed by cutting away the top surface portion 102a to form arcs.

As shown in FIGS. 1, 3, and 4, the two grooved portions 111A and 111B each have a first injection hole 112 and a second injection hole 113. First insertion holes 106 (see FIGS. 5 and 7) are formed in positions on the bottom surface portion 102c opposing the first injection holes 112. Second insertion holes 107 are formed in positions opposing the second injection holes 113. The first insertion holes 106 and the second insertion holes 107 extend through the bottom surface portion 102c in the up-down direction.

The first injection holes 112 and the first insertion holes 106 are positioned above the first reagent vessel 7a housed in the housing 101. The second injection holes 113 and the second insertion hole 107 are positioned above the second reagent vessel 7b. When sucking the first reagent housed in the first reagent vessel 7a, the probe 201 passes through the first injection hole 112 and the first insertion hole 106. When sucking the second reagent housed in the second reagent vessel 7b, the probe 201 passes through the second injection hole 113 and the second insertion hole 107.

As shown in FIG. 4, a first cap opening/closing device 120A and a second cap opening/closing device 120B that open and close the cap 71a of the first reagent vessel 7a and the cap 71b of the second reagent vessel 7b are provided at the bottom surface portion 102c of the cover member 102.

Next, a structure of the first cap opening/closing device 120A and a structure of the second cap opening/closing device 120B are described in detail with reference to FIGS. 5 to 8. Since the first cap opening/closing device 120A and the second cap opening/closing device 120B have the same structure, the structure of the first cap opening/closing device 120A is only described here.

Figure 5:
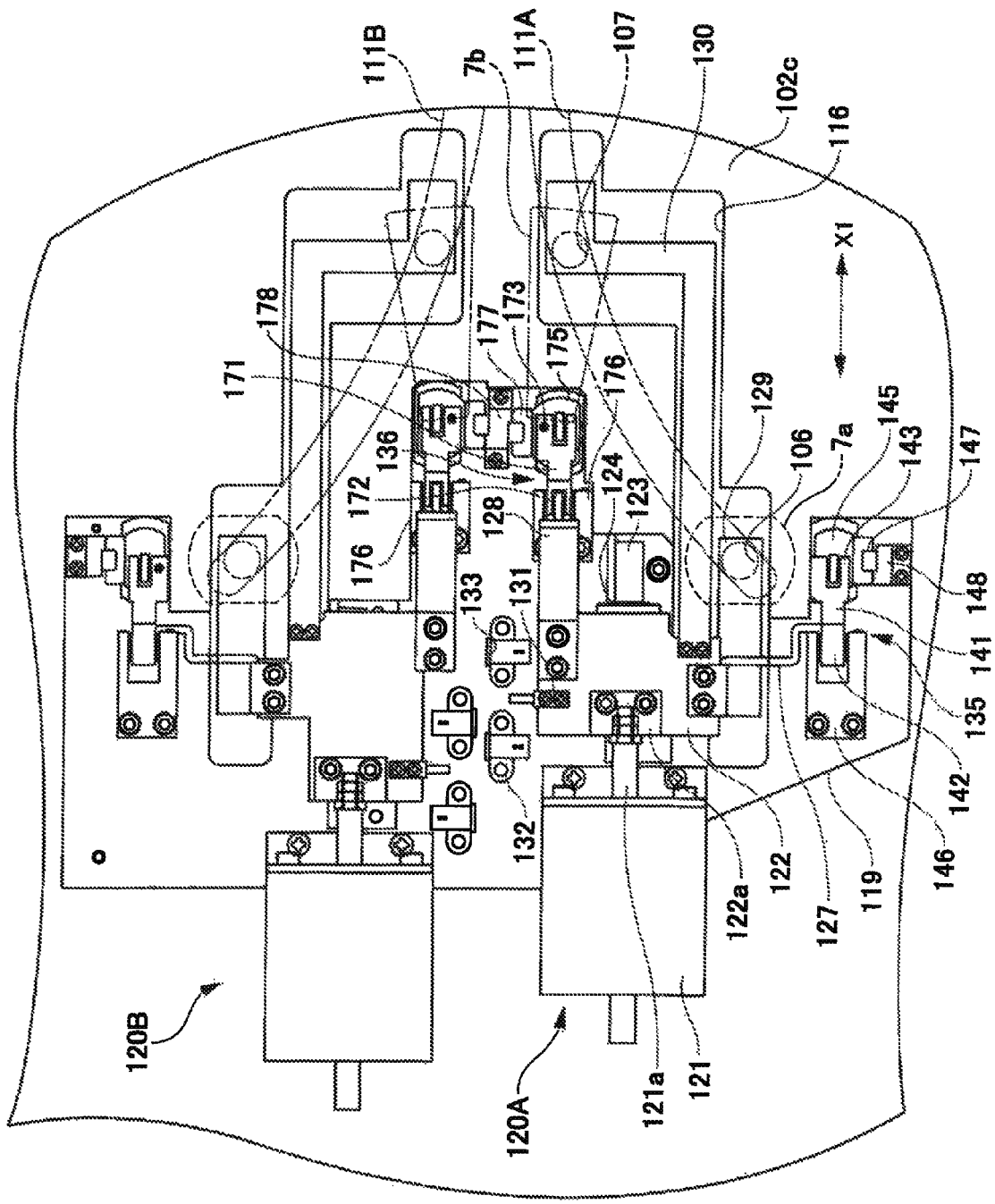
FIG. 5 is a plan view of a main portion of a cover member of the reagent vessel housing unit according to the embodiment of the present invention.
Figure 6:
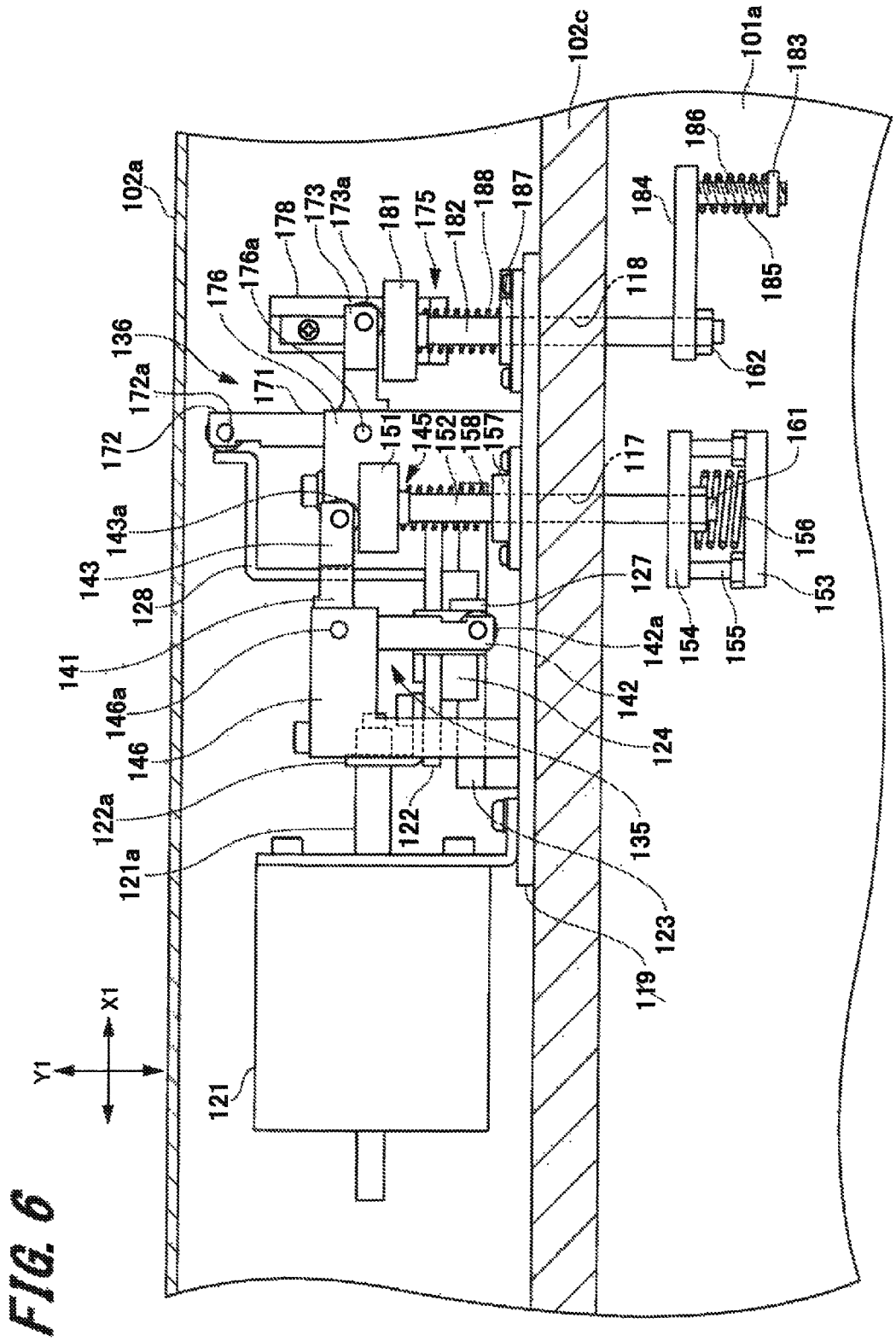
FIG. 6 is a side view of a main portion of the cover member of the reagent vessel housing unit according to the embodiment of the present invention.
Figure 7:
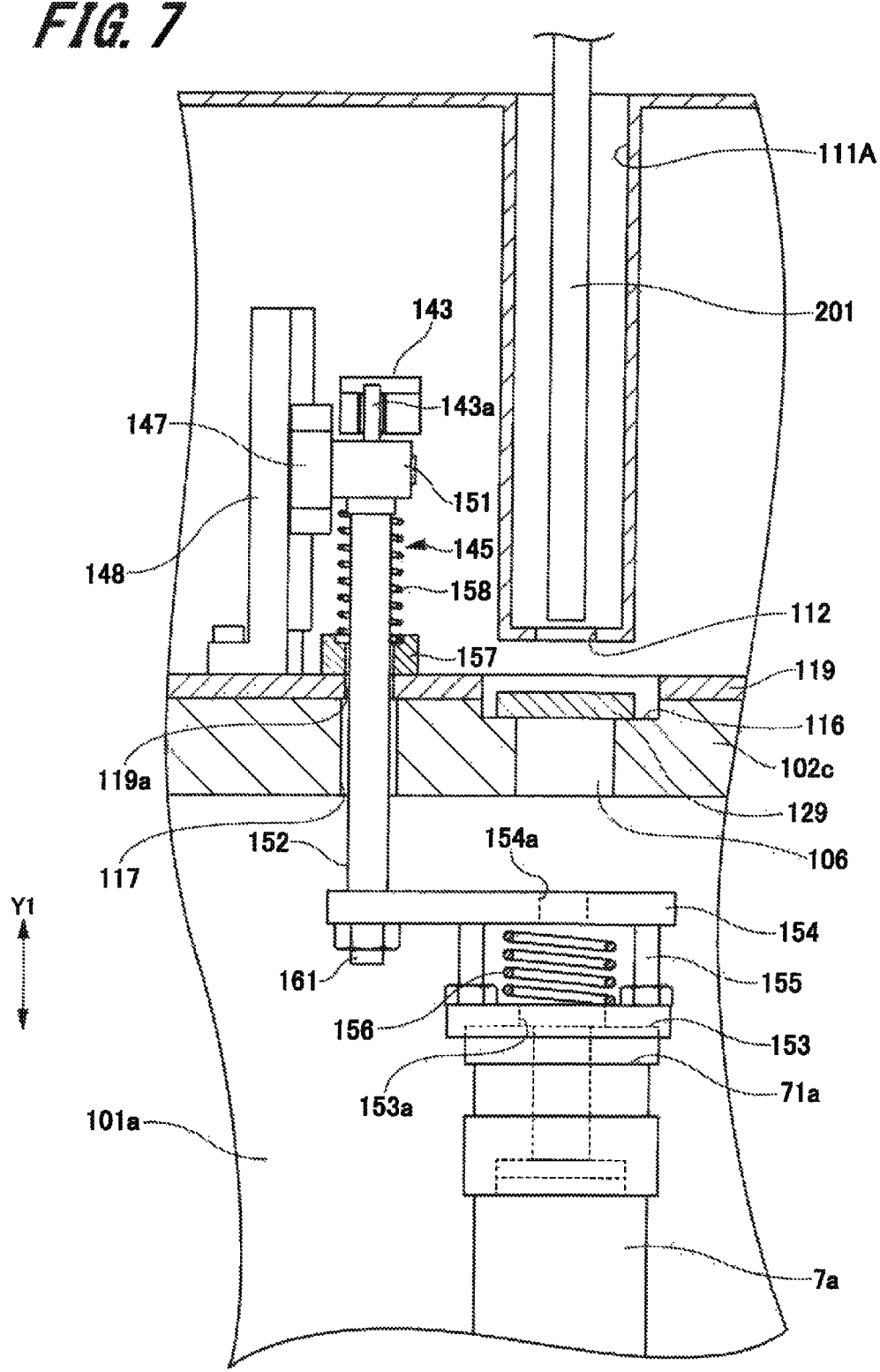
FIG. 7 is a sectional view of a first pusher member of the reagent vessel housing unit according to the embodiment of the present invention.
Figure 8:
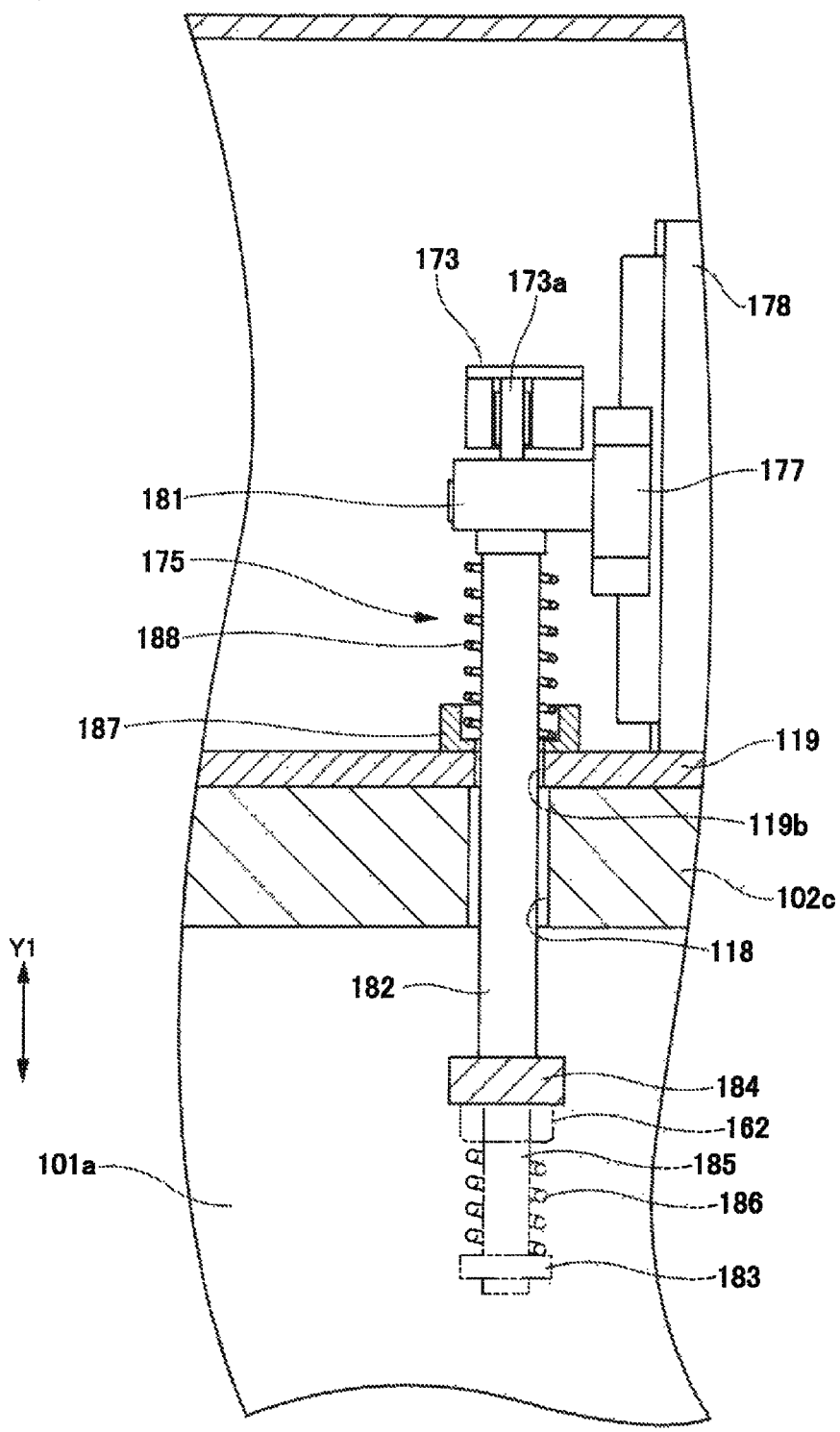
FIG. 8 is a sectional view of a second pusher member of the reagent vessel housing unit according to the embodiment of the present invention.

FIG. 5 is a plan view of the first cap opening/closing device 120A and the second cap opening/closing device 120B. FIG. 6 is a side view of the first cap opening/closing device 120A. FIGS. 7 and 8 are each a sectional view of a main portion of the first cap opening/closing device 120A.

As shown in FIG. 5, the first cap opening/closing device 120A and the second cap opening/closing device 120B are provided on a support base 119 fixed to a surface of the bottom surface portion 102c. The first cap opening/closing device 120A includes a drive unit 121, a base member 122, a guide rail 123, a slider 124, a first opening/closing mechanism 135, a second opening/closing mechanism 136, a first shutter member 129, a second shutter member 130, and a sensor piece 131.

The guide rail 123, a first sensor unit 132, and a second sensor unit 133 are fixed to the support base 119. The guide rail 123 is fixed to the support base 119 along a first direction X1 that is parallel to one surface of the bottom surface portion 102c. The slider 124 is supported so as to be slidable in the first direction X1 by the guide rail 123. The first sensor unit 132 is disposed closer to one side in the first direction X1 than the second sensor unit 133 is. As each of the first sensor unit 132 and the second sensor unit 133, for example, an optical sensor including a light emitting section that emits light and a light receiving section that receives the light emitted from the light emitting section is used.

A slide groove 116 is provided in the bottom surface portion 102c. The slide groove 116 is a recessed portion that is recessed by a predetermined depth from the one surface of the bottom surface portion 102c to the other surface of the bottom surface portion 102c. The slide groove 116 includes the first insertion hole 106 and the second insertion hole 107.

The drive unit 121 is a direct-driven motor including a shaft member 121a. The drive unit 121 causes the shaft member 121a to advance and retreat in the first direction X1. The base member 122 is fixed to one end portion of the shaft member 121a in an axial direction via a fixing member 122a.

The base member 122 is supported so as to be movable along the first direction X1 via the slider 124 by the guide rail 123. When the drive unit 121 is driven, the base member 122 moves from an initial position shown in FIG. 5 to a first opening position (see FIG. 9) at the one side in the first direction X1, and to a second opening position (see FIG. 11) at the other side in the first direction X1.

A first operating piece 127, a second operating piece 128, the first shutter member 129, the second shutter member 130, and the sensor piece 131 are fixed to the base member 122.

When the base member 122 is at the initial position, the sensor piece 131 is disposed between the first sensor unit 132 and the second sensor unit 133. When the base member 122 moves to the first opening position (see FIG. 9), the sensor piece 131 moves to a location between the light emitting section and the light receiving section of the first sensor unit 132, so that light from the light emitting unit is blocked. When the base member 122 moves to the second opening position (see FIG. 11), the sensor piece 131 moves to a location between the light emitting section and the light receiving section of the second sensor unit 133, so that light from the light emitting section is blocked. This makes it possible to determine whether the base member 122 has moved from the initial position to the first opening position (see FIG. 9) or to the second opening position (see FIG. 11).

Although, in the embodiment, an example in which an optical sensor is used as each of the first sensor unit 132 and the second sensor unit 133 is described, the present invention is not limited thereto. A mechanical sensor that performs mechanical switching between ON and OFF may be used.

As shown in FIGS. 5 and 6, the first operating piece 127 and the second operating piece 128 are each formed by bending a flat member. When the base member 122 is at the initial position, the first operating piece 127 contacts or separates from a first rotary member 141 of the first opening/closing mechanism 135 (described later), and the second operating piece 128 contacts or separates from a second rotary member 171 of the second opening/closing mechanism 136 (described later).

The first shutter member 129 and the second shutter member 130 are formed from substantially flat members. The first shutter member 129 and the second shutter member 130 are slidably placed in the slide groove 116 of the bottom surface portion 102c. When the base member 122 is at the initial position, the first shutter member 129 covers an opening of the first insertion hole 106 (see FIG. 7), and the second shutter member 130 covers an opening of the second insertion hole 107. This makes it possible to prevent cold air in the internal space 101a of the housing 101 (see FIG. 4) from flowing out to a side of the cover member 102 from the first insertion hole 106 and the second insertion hole 107, and to keep the temperature in the internal space 101a of the housing 101 at a predetermined temperature.

Further, by providing the slide groove 116 in which the first shutter member 129 and the second shutter member 130 slide, it is possible to prevent the first shutter member 129 and the second shutter member 130 from interfering with the grooved portion 111A. In addition, it is possible to reduce the length from the top surface portion 102a of the cover member 102 to the bottom surface portion 102c, and to thinly form the cover member 102. It is to be noted that even if the slide groove 116 is not provided, the object of the present invention can be realized.

[First Opening/Closing Mechanism]

The first opening/closing mechanism 135 is disposed at a side of the base member 122 where the first operating piece 127 is provided. The first opening/closing mechanism 135 includes the first rotary member 141, which is an exemplary first converting member, a supporting member 146 that rotatably supports the first rotary member 141, and a first pusher member 145.

The first rotary member 141 has a substantially L shape, and includes a first piece portion 142 and a second piece portion 143 that is substantially perpendicularly bent from the first piece portion 142. A roller 142a is rotatably provided at an end portion of the first piece portion 142, and a roller 143a is rotatably provided at an end portion of the second piece portion 143. The first rotary member 141 is such that an intermediate portion between the first piece portion 142 and the second piece portion 143, that is, a location of the first rotary member 141 where it is bent is rotatably supported by the supporting member 146 via a rotary shaft 146a. The roller 142a at the first piece portion 142 contacts or separates from the first operating piece 127. The roller 143a at the second piece portion 143 abuts upon a head portion 151 of the first pusher member 145 (described later). The first piece portion 142 is positioned closer to the one side in the first direction X1 than the first operating piece 127 is.

As shown in FIGS. 6 and 7, the first pusher member 145 includes, for example, the head portion 151, a shaft portion 152, a pushing portion 153, an adjusting plate 154, an adjusting screw 155, an adjusting spring 156, a spring bearing portion 157, and an urging spring 158. The shaft portion 152 extends through a through hole 119a of the support base 119 and a through hole 117 of the bottom surface portion 102c along a second direction Y, which is an up-down direction that is orthogonal to the first direction X1. One side of the shaft portion 152 in the second direction Y1 is exposed from the one surface of the bottom surface portion 102c to the interior of the cover member 102. The other side of the shaft portion 152 in the second direction Y1 is exposed from the other surface of the bottom surface portion 102c to a side of the internal space 101a of the housing 101. The head portion 151 is provided at the one side of the shaft portion 152 in the second direction Y1, that is, at a top portion thereof.

A rectilinear slider 147 is fixed to the head portion 151. The rectilinear slider 147 is slidably supported by a rectilinear guide 148. The rectilinear guide 148 is disposed along the second direction Y1 from the one surface of the bottom surface portion 102c. Therefore, the rectilinear slider 147 slides along the rectilinear guide 148 in the second direction Y1. This restricts movements of the first pusher member 145 in directions other than the second direction Y1, and allows the first pusher member 145 to move in the second direction Y1.

The spring bearing portion 157 through which the shaft portion 152 extends is fixed to the one surface of the bottom surface portion 102c. The urging spring 158 is interposed between the head portion 151 and the spring bearing portion 157. One end portion of the urging spring 158 in the second direction Y1 abuts upon the head portion 151, and the other end portion of the urging spring 158 in the second direction Y1 abuts upon the spring bearing portion 157. The urging spring 158 urges the head portion 151 towards one side in the second direction Y1.

The first pusher member 145 is such that the head portion 151 abuts upon the second piece portion 143 of the first rotary member 141 to restrict movement to one side in the second direction Y1. Therefore, it is possible to, by an urging force of the urging spring 158, prevent the first pusher member 145 from being dislodged from the through holes 119a and 117 to the one side in the second direction Y1.

The adjusting plate 154 is fixed to the other side of the shaft portion 152 in the second direction Y1, that is, a lower portion thereof, via a fixing screw 161. The flat pushing portion 153 is fixed to the adjusting plate 154 via the adjusting screw 155. The pushing portion 153 abuts upon the cap 71a of the first reagent vessel 7a. When the first pusher member 145 is pushed to the other side in the second direction Y1, that is, downward in the up-down direction, the pushing portion 153 pushes the cap 71a. When the cap 71a is pushed downward, the first reagent vessel 7a is such that a sealing member (not shown) in the cap 71a is pushed. The sealing member has a plurality of radially formed slits, and when pushed, the slits are uncovered.

The pushing portion 153 has a through hole 153a and the adjusting plate 154 has a through hole 154a, the probe 201 passing through the through holes 153a and 154a. The adjusting spring 156 is interposed between the pushing portion 153 and the adjusting plate 154. One end portion of the adjusting spring 156 in the second direction Y1 abuts upon the adjusting plate 154, and the other end portion of the adjusting spring 156 in the second direction Y1 abuts upon the pushing portion 153. The interval between the pushing portion 153 and the adjusting plate 154 in the second direction Y1 and an urging force of the adjusting spring 156 are adjusted on the basis of a tightening amount of the adjusting screw 155. This makes it possible to adjust a pushing force of the first pusher member 145 with respect to the cap 71a of the first reagent vessel 7a.

[Second Opening/Closing Mechanism]

As shown in FIGS. 5 and 6, the second opening/closing mechanism 136 is disposed at a side of the base member 122 where the second operating piece 128 is provided. The second opening/closing mechanism 136 includes the second rotary member 171, which is an exemplary second converting member, a supporting member 176 that rotatably supports the second rotary member, and a second pusher member 175.

The second rotary member 171 has a substantially L shape, and includes a first piece portion 172 and a second piece portion 173. A roller 172a is rotatably provided at an end portion of the first piece portion 172, and a roller 173a is rotatably provided at an end portion of the second piece portion 173. The second rotary member 171 is such that an intermediate portion between the first piece portion 172 and the second piece portion 173, that is, a location of the second rotary member 171 where it is bent, is rotatably supported by the supporting member 176 via a rotary shaft 176a. The roller 172a at the first piece portion 172 abuts upon the second operating piece 128. The roller 173a at the second piece portion 173 abuts upon a head portion 181 of the second pusher member 175 (described later). The first piece portion 172 is positioned closer to the other side in the first direction X1 than the second operating piece 128 is.

As shown in FIGS. 6 and 8, the second pusher member 175 includes, for example, the head portion 181, a shaft portion 182, an adjusting nut 183, an adjusting plate 184, an adjusting screw 185, an adjusting spring 186, a spring bearing portion 187, and an urging spring 188. The shaft portion 182 extends through a through hole 119b of the support base 119 and a through hole 118 of the bottom surface portion 102c along the second direction Y. One side of the shaft portion 182 in the second direction Y1 is exposed from the one surface of the bottom surface portion 102c to the interior of the cover member 102. The other side of the shaft portion 182 in the second direction Y1 is exposed from the other surface of the bottom surface portion 102c to the side of the internal space 101a of the housing 101. The head portion 181 is provided at the one side of the shaft portion 182 in the second direction Y1, that is, at a top portion thereof.

A rectilinear slider 177 is fixed to the head portion 181. The rectilinear slider 177 is slidably supported by a rectilinear guide 178. The rectilinear guide 178 is disposed along the second direction Y1 from the one surface of the bottom surface portion 102c. Therefore, the rectilinear slider 177 slides along the rectilinear guide 178 in the second direction Y1. This restricts movements of the second pusher member 175 in directions other than the second direction Y1, and allows the second pusher member 175 to move in the second direction Y1.

The spring bearing portion 187 through which the shaft portion 182 extends is fixed to the one surface of the bottom surface portion 102c. As in the first pusher member 145, the urging spring 188 is interposed between the head portion 181 and the spring bearing portion 187. The structure of the urging spring 188 is the same as the structure of the urging spring 158 of the first pusher member 145, and, thus, is not described.

The adjusting plate 184 is fixed to the other side of the shaft portion 182 in the second direction Y1, that is, a lower portion thereof, via a fixing screw 162. The adjusting screw 185, which is an exemplary pushing portion, is fixed to the adjusting plate 184. The other end of the adjusting screw 185 in the second direction Y1 pushes the cap 71b of the second reagent vessel 7b (see FIG. 4).

The adjusting nut 183 is provided at the other side of the adjusting screw 185 in the second direction Y1. The adjusting spring 186 is interposed between the adjusting nut 183 and the adjusting plate 184. The adjusting spring 186 is disposed at an outer side of the adjusting screw 185 in a peripheral direction thereof. One end portion of the adjusting spring 186 in the second direction Y1 abuts upon the adjusting plate 184, and the other end portion of the adjusting spring 186 in the second direction Y1 abuts upon the adjusting nut 183. An urging force of the adjusting spring 186 is adjusted by adjusting a tightening amount of the adjusting nut 183. This makes it possible to adjust a pushing force of the adjusting screw 185 with respect to the cap 71b by adjusting the urging force of the adjusting spring 186.

2. Operation of Reagent Vessel Housing Unit

Next, operations of the above-described reagent vessel housing unit 7 are described with reference to FIGS. 9 to 12.

FIGS. 9 to 12 are each an explanatory view of an operation of the reagent vessel housing unit 7.

First, the operation of the reagent vessel housing unit 7 when the probe sucks the first reagent in the first reagent vessel 7a is described with reference to FIGS. 9 and 10.

Figure 9:
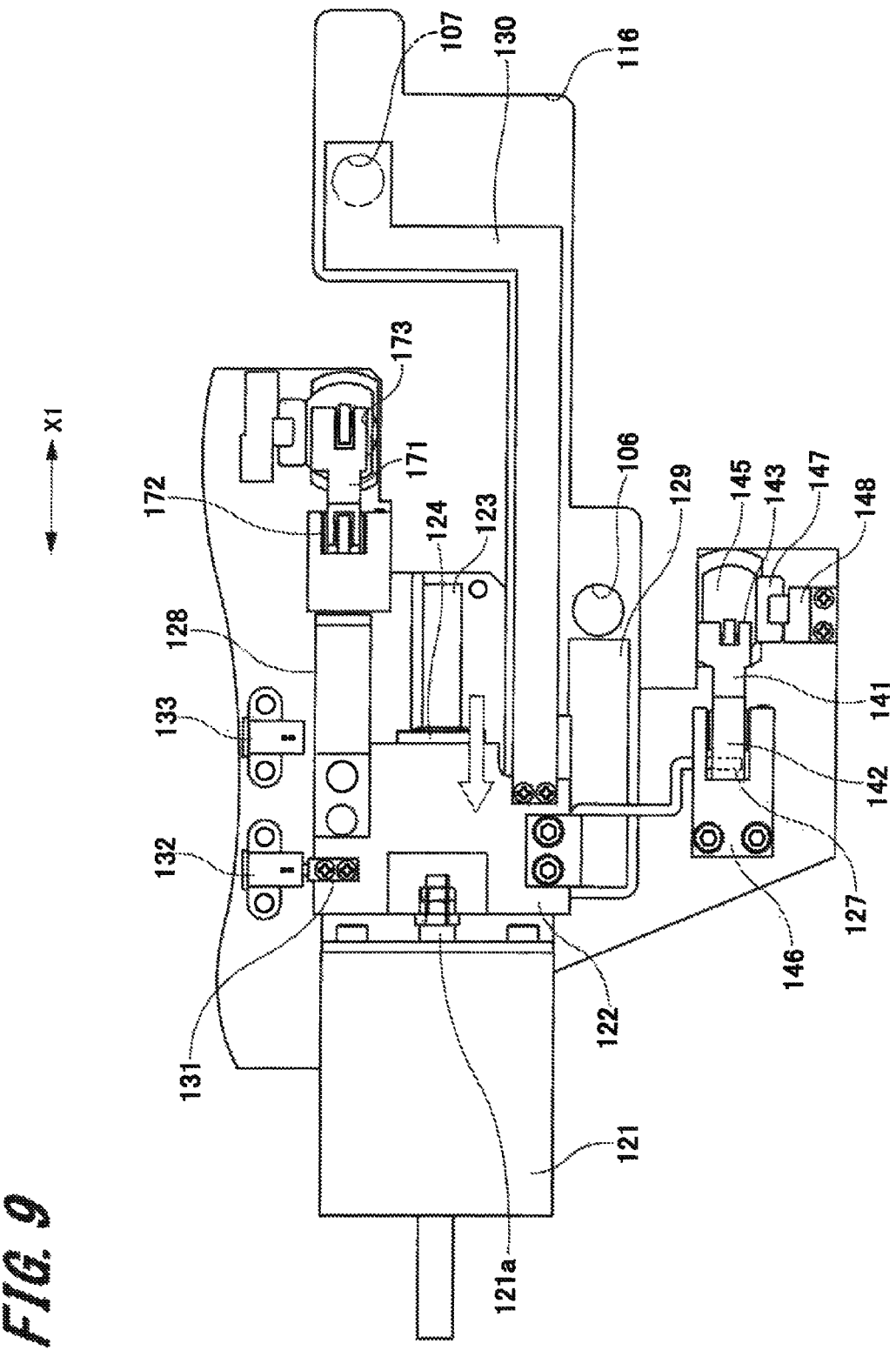
FIG. 9 is a plan view illustrating an operation of the reagent vessel housing unit according to the embodiment of the present invention.
Figure 10:
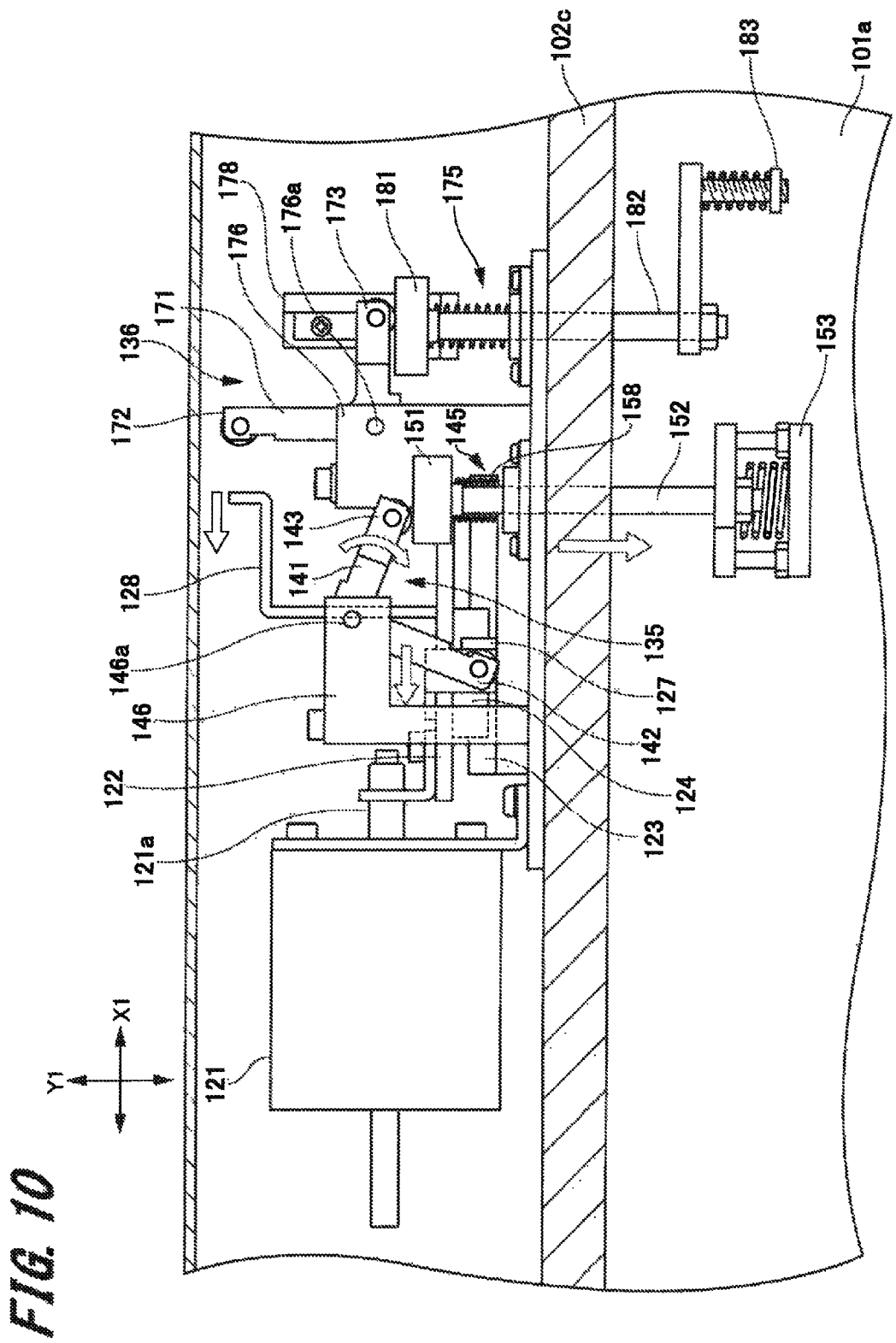
FIG. 10 is a side view illustrating an operation of the reagent vessel housing unit according to the embodiment of the present invention.

When the probe 201 passes through the grooved portion 111A, and moves to a location above the first injection hole 112 and the first insertion hole 106, as shown in FIGS. 9 and 10, the drive unit 121 is driven, and the shaft member 121a moves to the one side in the first direction X1. By moving the shaft member 121a to the one side in the first direction X1, the base member 122 moves along the guide rail 123 from the initial position to the first opening position. By moving the sensor piece 131 to a location between the light emitting section and the light receiving section of the first sensor unit 132, the first sensor unit 132 detects that the base member 122 has moved from the initial position to the first opening position.

As the base member 122 moves, the first operating piece 127, the second operating piece 128, the first shutter member 129, and the second shutter member 130, which are fixed to the base member 122, move to the one side in the first direction X1. Therefore, as shown in FIG. 9, the opening of the first insertion hole 106 that had been covered by the first shutter member 129 is uncovered. The opening of the second insertion hole 107 is covered by the second shutter member 130. This makes it possible to prevent cold air in the internal space 101a of the housing 101 from flowing out to the side of the cover member 102 from the second insertion hole 107 where suction is not performed.

Further, by moving the first operating piece 127 to the one side in the first direction X1, as shown in FIG. 10, the first piece portion 142 of the first rotary member 141 of the first opening/closing mechanism 135 is pushed by the first operating piece 127 to the one side in the first direction X1. The first rotary member 141 is rotatably supported by the supporting member 146 via the rotary shaft 146a. Therefore, the first rotary member 141 rotates around the rotary shaft 146a as center. That is, the direction of a driving force of the drive unit 121 is converted from the first direction X1 to the second direction Y1 by the first rotary member 141.

By rotating the first rotary member 141, the second piece portion 143 moves to the other side in the second direction Y. The second piece portion 143 opposes the urging force of the urging spring 158 of the first pusher member 145, and pushes the head portion 151 to the other side in the second direction Y1. At this time, since movements of the head portion 151 in directions other than the second direction Y1 are restricted by the rectilinear guide 148, the head portion 151 and the shaft portion 152 move along the second direction Y1. As a result, the cap 71a of the first reagent vessel 7a (see FIG. 7) is pushed by the pushing portion 153 of the first pusher member 145, so that the first reagent vessel 7a is uncovered.

Next, when the probe 201 moves to the other side in the second direction Y1, the probe 201 passes through the first injection hole 112 and the first insertion hole 106. That is, the probe 201 extends through the bottom surface portion 102c from the upper surface portion 102a of the cover member 102, and reaches the internal space 101a of the housing 101. Then, the first reagent housed in the first reagent vessel 7a is sucked by the probe 201.

As shown in FIGS. 9 and 10, when the second operating piece 128 moves to the one side in the first direction X1, the second operating piece 128 separates from the first piece portion 172 of the second rotary member 171 of the second opening/closing mechanism 136. Therefore, the second rotary member 171 of the second opening/closing mechanism 136 does not rotate, and the second pusher member 175 remains at the initial position. As a result, the cap 71b of the second reagent vessel 7b remains closed.

Next, when the suction of the first reagent by the probe 201 is completed, and the probe 201 retreats to a location above the first injection hole 112 (the one side in the second direction Y1), the drive unit 121 is driven, and the base member 122 moves to the initial position shown in FIGS. 5 and 6 from the first opening position. Therefore, the first shutter member 129 moves to the other side in the first direction X1, and the opening of the first insertion hole 106 is covered again. Further, by moving the first operating piece 127 to the other side in the first direction X1, the pushing against the first rotary member 141 is stopped. Then, by the urging force of the urging spring 158 of the first pusher member 145, the first pusher member 145 moves to the one side in the second direction Y1, and the head portion 151 pushes the second piece portion 143 of the first rotary member 141 to the one side in the second direction Y1. As a result, the first rotary member 141 rotates in a direction opposite to the direction shown in FIG. 10, and returns to the initial position shown in FIGS. 5 and 6. The pushing against the cap 71a of the first reagent vessel 7a is stopped, and the first reagent vessel 7a is covered by the cap 71a.

Figure 11:
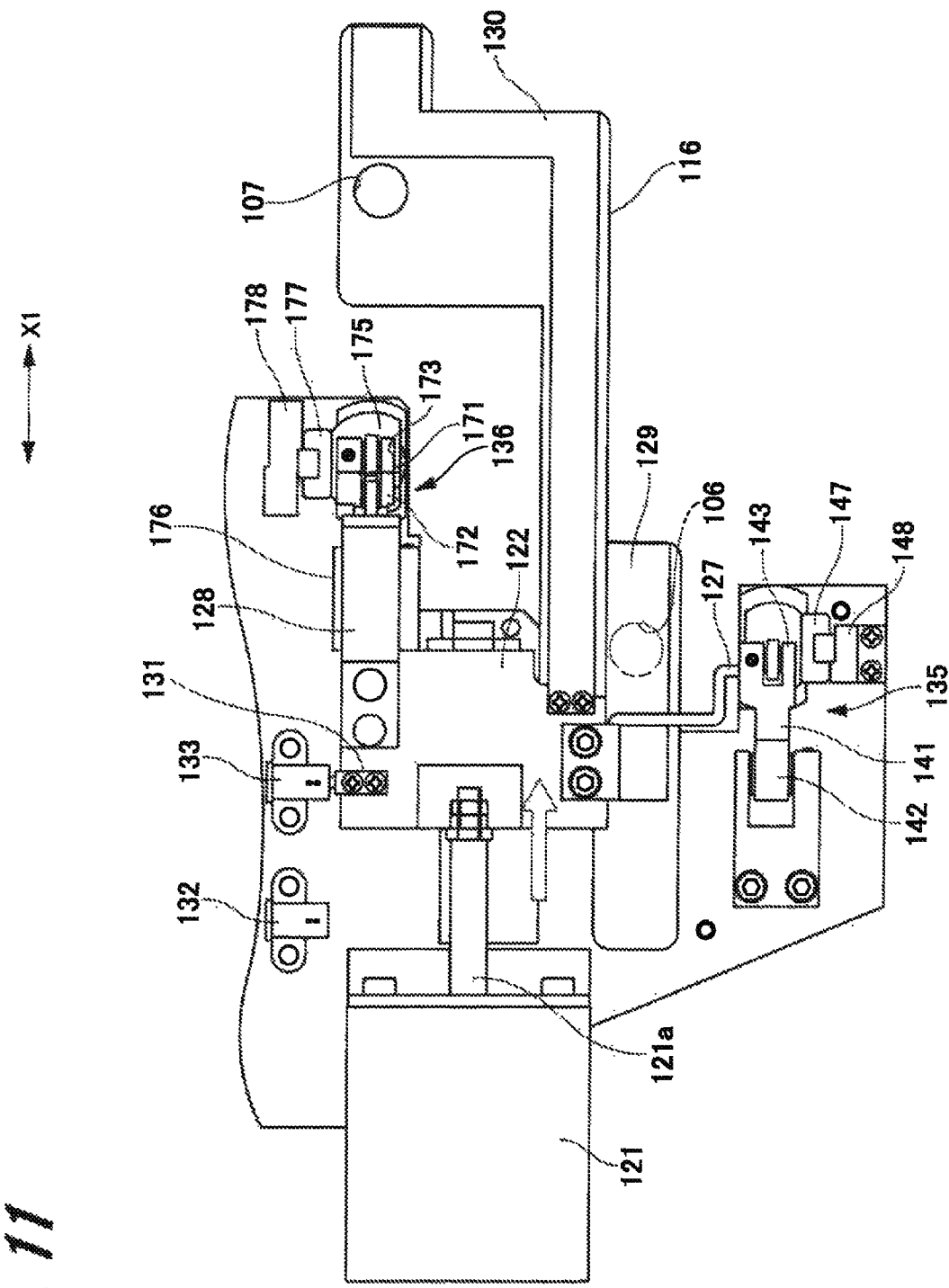
FIG. 11 is a plan view illustrating an operation of the reagent vessel housing unit according to the embodiment of the present invention.
Figure 12:
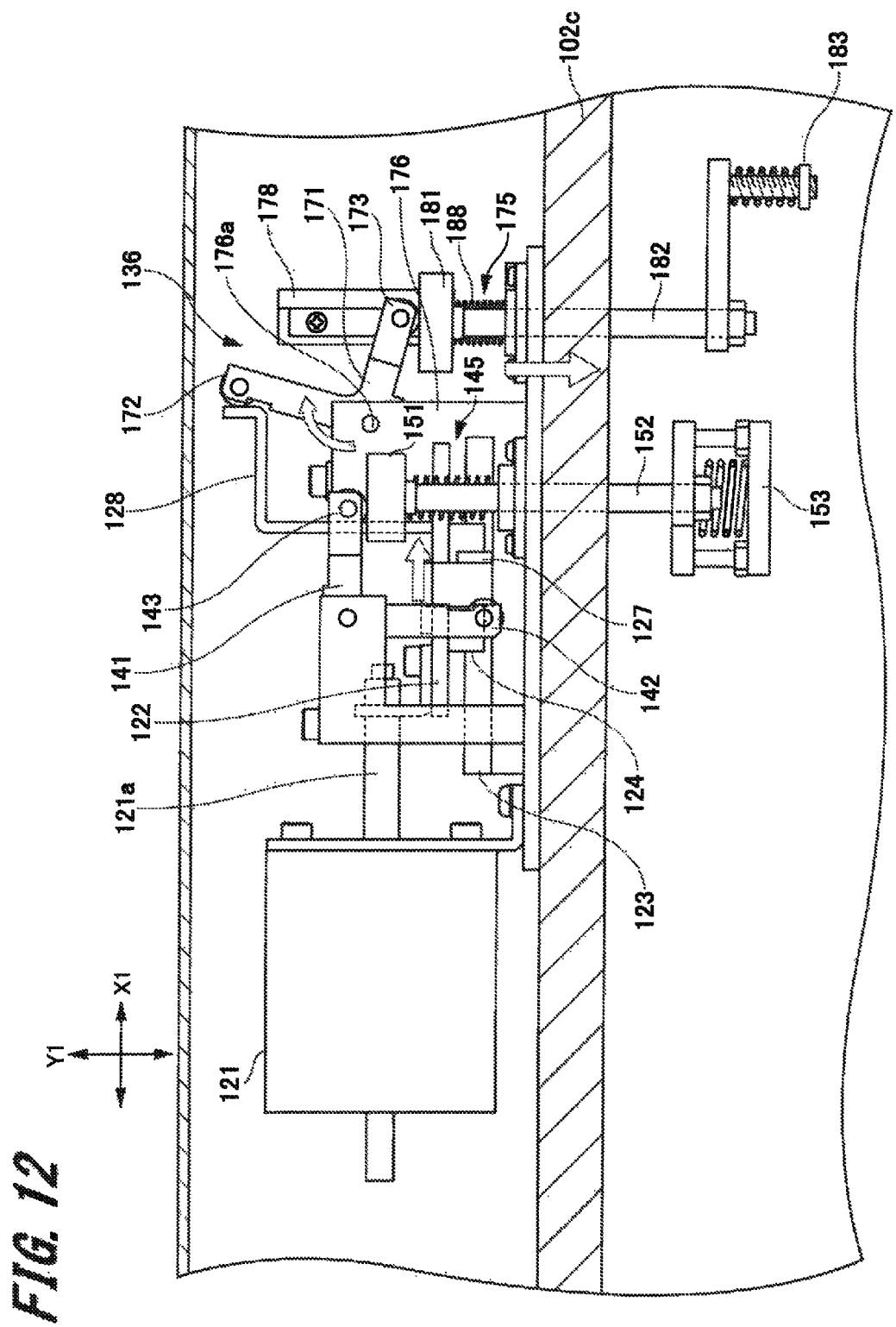
FIG. 12 is a side view illustrating an operation of the reagent vessel housing unit according to the embodiment of the present invention.

Next, when the probe 201 passes through the grooved portion 111A, and moves to a location above the second injection hole 113 and the second insertion hole 107, as shown in FIGS. 11 and 12, the drive unit 121 is driven, and the shaft member 121a moves to the other side in the first direction X1. In addition, the base member 122 secured to the shaft member 121a moves to the second opening position from the initial position. By moving the sensor piece 131 to a location between the light emitting section and the light receiving section of the second sensor unit 133, the second sensor unit 133 detects that the base member 122 has moved to the second opening position from the initial position.

As the base member 122 moves, the first operating piece 127, the second operating piece 128, the first shutter member 129, and the second shutter member 130, which are fixed to the base member 122, move to the other side in the first direction X1. Therefore, as shown in FIG. 11, the opening of the second insertion opening 107 that had been covered by the second shutter member 130 is uncovered. The opening of the first insertion hole 106 is covered by the first shutter member 129. This makes it possible to prevent cold air in the internal space 101a of the housing 101 from flowing out to the side of the cover member 102 from the first insertion hole 106 where suction is not performed.

Further, by moving the second operating piece 128 to the one side in the first direction X1, as shown in FIG. 12, the first piece portion 172 of the second rotary member 171 of the second opening/closing mechanism 136 is pushed by the second operating piece 128 to the other side in the first direction X1. The second rotary member 171 is rotatably supported by the supporting member 176 via the rotary shaft 176a. Therefore, the second rotary member 171 rotates around the rotary shaft 176a as center. That is, the direction of a driving force of the drive unit 121 is converted from the first direction X1 to the second direction Y1 by the second rotary member 171.

By rotating the second rotary member 171, the head portion 181 of the second pusher member 175 is pushed to the other side in the second direction Y by the second piece portion 173 of the second rotary member 171. Similarly to the first pusher member 145, movements of the second pusher member 175 in directions other than the second direction Y1 are restricted by the rectilinear guide 178. The second pusher member 175 opposes an urging force of the urging spring 188, and moves to the other side in the second direction Y1. As a result, the cap 71b of the second reagent vessel 7b (see FIG. 4) is pushed by the adjusting screw 185 of the second pusher member 175, so that the second reagent vessel 7b is uncovered.

When the first operating piece 127 moves to the other side in the first direction X1, the first operating piece 127 separates from the first piece portion 142 of the first rotary member 141 of the first opening/closing mechanism 135. Therefore, the first rotary member 141 of the first opening/closing mechanism 135 does not rotate. In addition, the first pusher member 145 remains at the initial position, and the cap 71a of the first reagent vessel 7a remains closed.

The cap 71b of the second reagent vessel 7b can be closed by returning the base member 122 to the initial position from the second opening position.

According to the reagent vessel housing unit 7 of the embodiment, it is possible to open and close the caps 71a and 71b of the two respective reagent vessels 7a and 7b and uncover and cover the two insertion holes 106 and 107 by using one drive unit 121. This makes it possible to reduce the number of drive units 121, save electric power, and reduce the weight of the cover member 102. In addition, it is possible to reduce the number of components. Further, it is possible to independently open and close the cap 71a of the first reagent vessel 7a and the cap 71b of the second reagent vessel 7b as a result of moving the base member 122 to three positions, that is, the initial position, the first opening position, and the second opening position.

The present invention is not limited to the above-described embodiment illustrated in the drawings. Various modifications may be made within a scope that does not depart from the gist of the invention described in the claims. For example, although, in the above-described embodiment, an example in which the first shutter member 129 that covers the first insertion hole 106 and the second shutter member 130 that covers the second insertion hole 107 are formed as separate members is described, the first shutter member 129 and the second shutter member 130 may be integrated with each other.

Although, in the above-described embodiment, an example in which the cap 71a of the first reagent vessel 7a and the cap 71b of the second reagent vessel 7b are opened and closed by pushing the caps 71a and 71b is described, the present invention is not limited thereto. The cap of the first reagent vessel 7a and the cap of the second reagent vessel 7b may be opened and closed by sliding the caps in the first direction X1. In this case, the first opening/closing mechanism and the second opening/closing mechanism are operated by the base member and are slid along the first direction X1 to slide the cap of the first reagent vessel and the cap of the second reagent vessel.

Further, although an example in which, as the automatic analysis device, an immunology device that performs immunology tests is used is described, the present invention is not limited thereto. For example, a biochemical analysis device that is used in analyzing biological samples, such as blood or urine, or devices that perform various other types of analyses, such as a water analysis or a food analysis, may be used.

REFERENCE SIGNS LIST 1 automatic analysis device
2 measuring device
7 reagent vessel housing unit
10 immune enzyme reaction unit (reaction unit)
7a first reagent vessel
7b second reagent vessel
71a, 71b cap
101 housing
101a internal space
102 cover member
102a top surface portion
102b side surface portion
102c bottom surface portion
103 turntable
104 table drive mechanism
106 first insertion hole
107 second insertion hole
111A, 111B grooved portion
112 first injection hole
113 second injection hole
116 slide groove
119 support base
120A, 120B cap opening/closing device
121 drive unit
121a shaft member
122 base member
122a fixing member
123 guide rail
124 slider
127 first operating piece
128 second operating piece
129 first shutter member
130 second shutter member
131 sensor piece
132 first sensor unit
133 second sensor unit
135 first opening/closing mechanism
136 second opening/closing mechanism
141 first rotary member
142, 172 first piece portion
143, 173 second piece portion
145 first pusher member
146 supporting member
146a rotary shaft
147 rectilinear slider
148 rectilinear guide
151, 181 head portion
152, 182 shaft portion
153, 185 pushing portion
171 second rotary member
175 second pusher member X1 first direction
Y1 second direction
201 probe

The invention claimed is:

1. A reagent vessel housing unit comprising:
a housing that houses a first reagent vessel and a second reagent vessel and that has an opening portion, the first reagent vessel and the second reagent vessel each having a cap;
a hollow cover member that includes a bottom surface portion that covers the opening portion of the housing;
a drive unit disposed in the cover member;
a base member that is movable to an initial position, a first opening position, and a second opening position by a driving force of the drive unit, the initial position being where the cap of the first reagent vessel and the cap of the second reagent vessel are closed, the first opening position being where the cap of the first reagent vessel is opened, the second opening position being where the cap of the second reagent vessel is opened;
a first opening/closing mechanism that is operated by the base member and that opens the cap of the first reagent vessel when the base member has moved to the first opening position;
a second opening/closing mechanism that is operated by the base member and that opens the cap of the second reagent vessel when the base member has moved to the second opening position; and
means for controlling the drive unit to position the base member at the initial position, first opening position, or second opening position,
wherein the base member is provided with:
a first operating piece that abuts upon the first opening/closing mechanism; and
a second operating piece that abuts upon the second opening/closing mechanism,
wherein, when the base member has moved to the first opening position from the initial position, the first opening/closing mechanism is pushed by the first operating piece, and when the base member has moved to the second opening position from the initial position, the first operating piece separates from the first opening/closing mechanism, and
wherein, when the base member has moved to the second opening position from the initial position, the second opening/closing mechanism is pushed by the second operating piece, and, when the base member has moved to the first opening position from the initial position, the second operating piece separates from the second opening/closing mechanism.

2. The reagent vessel housing unit according to claim 1, comprising a guide rail that supports the base member so as to be movable in a first direction that is parallel to the bottom surface portion,
wherein the cap of the first reagent vessel and the cap of the second reagent vessel are opened by being pushed in a second direction that is orthogonal to the first direction,
wherein the first opening/closing mechanism includes
a first converting member that contacts or separates from the first operating piece, and that converts a movement force at the first operating piece from the first direction to the second direction, and
a first pusher member that is pushed by the first converting member and that pushes the cap of the first reagent vessel, and wherein the second opening/closing mechanism includes
a second converting member that contacts or separates from the second operating piece, and that converts a movement force at the second operating piece from the first direction to the second direction, and
a second pusher member that is pushed by the second converting member and that pushes the cap of the second reagent vessel.

3. The reagent vessel housing unit according to claim 2, wherein the first converting member is formed from an L-shaped first rotary member including a first piece portion that contacts or separates from the first operating piece and a second piece portion that is perpendicularly bent from the first piece portion and that contacts the first pusher member,
wherein the second converting member is formed from an L-shaped second rotary member including a first piece portion that contacts or separates from the first operating piece and a second piece portion that is perpendicularly bent from the first piece portion and that contacts the second pusher member, and
wherein a supporting member that rotatably supports the first rotary member and a supporting member that rotatably supports the second rotary member are provided at the bottom surface portion of the cover member.

4. The reagent vessel housing unit according to any one of claims 1 and 2 to 3,
wherein the cover member has
a first insertion hole in a position at the bottom surface portion where a first reagent housed in the first reagent vessel is sucked, a probe that sucks the first reagent being inserted into the first insertion hole, and
a second insertion hole in a position at the bottom surface portion where a second reagent housed in the second reagent vessel is sucked, the probe that sucks the second reagent being inserted into the second insertion hole,
wherein the reagent vessel housing unit further comprises
a first shutter that is provided at the base member and that covers the first insertion hole; and
a second shutter member that is provided at the base member and that covers the second insertion hole,
wherein, when the base member has moved to the first opening position from the initial position, the first shutter member uncovers an opening of the first insertion hole, and
wherein, when the base member has moved to the second opening position from the initial position, the second shutter member uncovers an opening of the second insertion hole.

5. An automatic analysis device comprising:
a reagent vessel housing unit that houses a first reagent vessel that houses a first reagent and a second reagent vessel that houses a second reagent; and
a reaction unit that sucks the first reagent and the second reagent and that causes a reaction of the first reagent and the second reagent with a sample to occur,
wherein the reagent vessel housing unit includes:
a housing that houses a first reagent vessel and a second reagent vessel and that has an opening portion, the first reagent vessel and the second reagent vessel each having a cap;
a hollow cover member that includes a bottom surface portion that covers the opening portion of the housing;

a drive unit disposed in the cover member;

a detector to measure an emission quantity of light generated from an immune complex that is generated when a reagent and a sample react with each other;

a base member that is movable to an initial position, a first opening position, and a second opening position by a driving force of the drive unit, the initial position being where the cap of the first reagent vessel and the cap of the second reagent vessel are closed, the first opening position being where the cap of the first reagent vessel is opened, the second opening position being where the cap of the second reagent vessel is opened;

a first opening/closing mechanism that is operated by the base member and that opens the cap of the first reagent vessel when the base member has moved to the first opening position;

a second opening/closing mechanism that is operated by the base member and that opens the cap of the second reagent vessel when the base member has moved to the second opening position; and means for controlling the drive unit to position the base member at the initial position, first opening position, or second opening position, wherein the base member is provided with:

a first operating piece that abuts upon the first opening/closing mechanism; and a second operating piece that abuts upon the second opening/closing mechanism, wherein, when the base member has moved to the first opening position from the initial position, the first opening/closing mechanism is pushed by the first operating piece, and when the base member has moved to the second opening position from the initial position, the first operating piece separates from the first opening/closing mechanism, and wherein, when the base member has moved to the second opening position from the initial position, the second opening/closing mechanism is pushed by the second operating piece, and when the base member has moved to the first opening position from the initial position, the second operating piece separates from the second opening/closing mechanism.

* * * * *